United States Patent [19]

Agarwal et al.

[11] 4,096,859

[45] Jun. 27, 1978

[54] APPARATUS FOR PERITONEAL DIALYSIS

[76] Inventors: Mahesh C. Agarwal, 6040 Bathurst St., Suite 1707, Toronto, Ontario M2R 2A1; Joseph E. Dadson, 2515 Bathurst St., Suite #503, Toronto, Ontario, both of Canada

[21] Appl. No.: 784,416

[22] Filed: Apr. 4, 1977

[51] Int. Cl.$^2$ .......................... A61J 7/00; B01D 13/00; A61M 5/00
[52] U.S. Cl. .................................. 128/213; 210/321 A
[58] Field of Search ..................... 210/321 B, 321 A; 128/214 R, 213, 214 E, DIG. 3, DIG. 13

[56] References Cited

U.S. PATENT DOCUMENTS

| 3,545,438 | 12/1970 | DeVries | 128/213 |
| 3,620,215 | 11/1971 | Tysk | 128/213 |
| 3,709,222 | 1/1973 | DeVries | 128/213 |
| 3,872,863 | 3/1975 | Lasker et al. | 128/214 E |
| 3,902,490 | 9/1975 | Jacobsen et al. | 128/DIG. 3 |
| 3,908,653 | 9/1975 | Kettering | 128/DIG. 3 |
| 3,946,731 | 3/1976 | Lichtenstein | 128/DIG. 3 |

FOREIGN PATENT DOCUMENTS

| 1,964,734 | 7/1971 | Germany | 128/213 |
| 1,964,735 | 7/1971 | Germany | 128/213 |

Primary Examiner—Frank A. Spear, Jr.
Assistant Examiner—E. Rollins Cross
Attorney, Agent, or Firm—Sim & McBurney

[57] ABSTRACT

This invention relates to a dialysis apparatus having means for supplying dialysis fluid to the peritoneal cavity of a patient and for draining the fluid from the cavity. Valve means are provided to permit a "FILL", a "DWELL", and a "DRAIN" phase to be carried out each cycle. The valve means includes individually occluding cams which control fluid flow through individual tubes.

18 Claims, 9 Drawing Figures

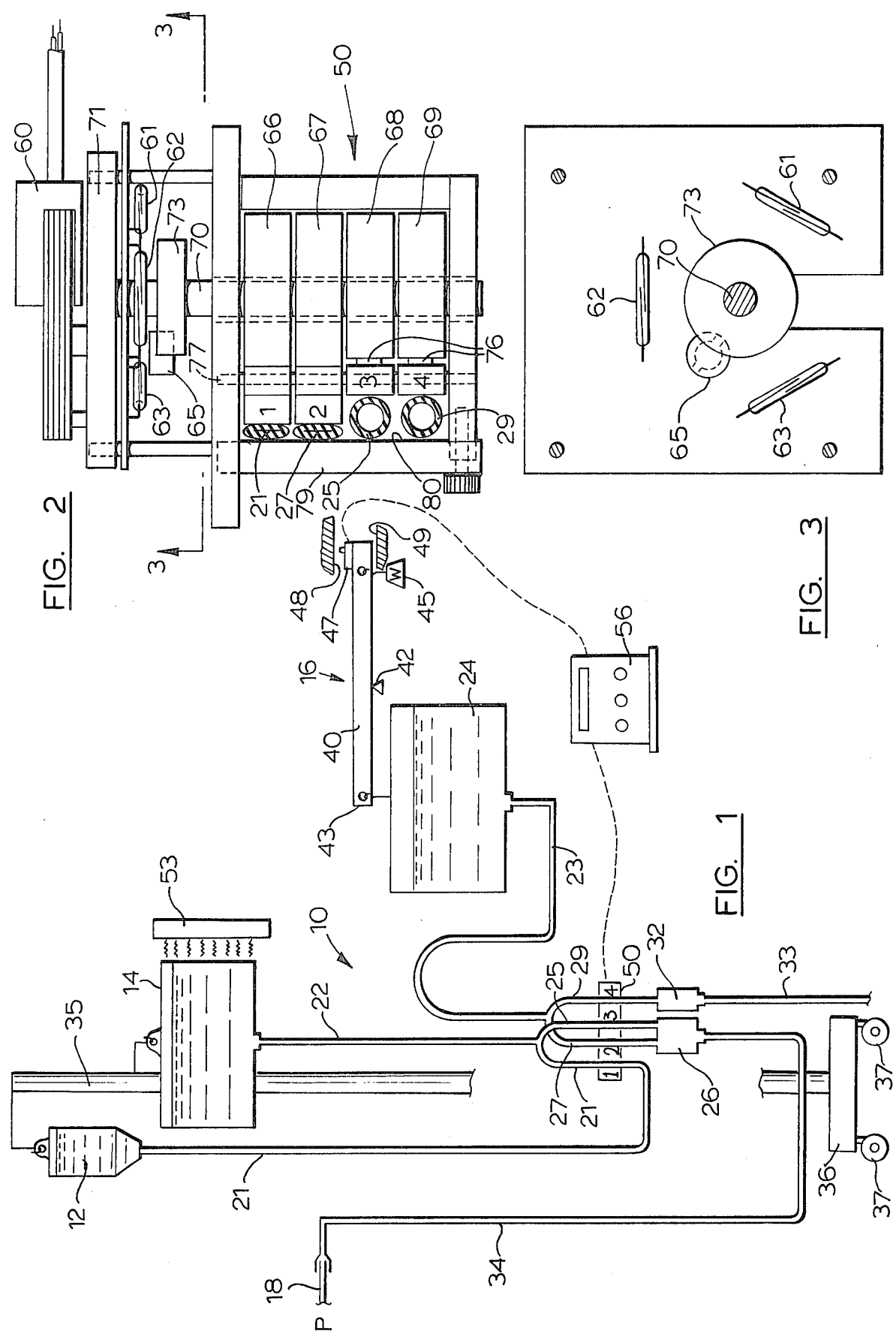

APPARATUS FOR PERITONEAL DIALYSIS

This invention relates to a method and apparatus for performing peritoneal dialysis, capable of use in both the hospital and home environment.

Peritoneal dialysis can be used for correcting the following medical disorders:
1. Acute and chronic renal failure
2. Severe water retention
3. Electrolyte disorders and
4. Drug intoxication (acute poisoning).

The normal function of the kidneys is to excrete metabolic waste products from the body. The kidneys also regulate accurately the amount and composition of body fluids. The kidneys perform important endocrine functions as well, some of which are blood pressure regulation, bone marrow function, and bone composition and turnover.

In kidney failure the above functions are affected to varying degrees. When kidney failure is mild or moderate, some of the resulting abnormalities can be corrected or ameliorated by drugs or dietary measures. When the kidney failure is severe however, artificial kidney function becomes necessary to maintain life. Artificial kidney (dialysis) treatment cannot totally compensate for the patient's own kidneys. Dialysis primarily substitutes for the lost excretory function and helps regulate fluid, electrolyte and acid-base balance.

There are two types of artificial kidney treatment, namely hemodialysis and peritoneal dialysis.

Hemodialysis is a direct treatment of the blood using an extra-corporeal system with an artificial membrane (kidney), while peritoneal dialysis uses the principles of osmosis and diffusion across the peritoneal membrane to indirectly remove toxic substances from the blood, and thereby correct certain electrolyte and fluid imbalances. As a result, extra-corporeal hemodialysis is used when rapid and efficient dialysis is necessary to preserve the life of the patient in cases of severe renal failure or drug intoxication.

Hemodialysis is technically more demanding than peritoneal dialysis, and this along with other medical reasons has led to increasing use of the relatively simple peritoneal operation for (a) acute and chronic renal failure, (b) severe water retention, (c) electrolyte disorders and (d) drug intoxication (acute poisoning).

Until recently peritoneal dialysis treatment was a manual operation. Current peritoneal dialysis instrumentation falls into two categories: (a) complete automatic fluid proportioning system, and (b) simple semi-automatic cycler. The peritoneal automatic fluid proportioning units are technically as complicated as the hemodialysis machines. The semi-automatic cycler system requires the least amount of technical operating skill, and operates under the principles of gravity and siphon. This system, commonly called "cycler", allows the dialysis fluid to flow into the abdominal cavity under gravitational action, keeps it in there for a period of time, and then allows the fluid to flow out. This cycle is continuously repeated until the end of the dialysis treatment.

One of the currently utilized peritoneal dialysis cyclers lacks many important features necessary for efficient dialysis, reliability and patient safety. This cycler is mostly a mechanical unit employing several moving parts which lead to frequent breakdowns. The prior art design is based on a two-mode selection, namely FILL and DRAIN, and this limits the efficiency and speed of dialysis. It also affects the operating temperature of the dialysis solution. Generally speaking, there is some difficulty in ensuring that the temperature of the dialysis solution prior to entering the patient's body has reached the required level.

It is an aspect of the present invention to provide an improved method and apparatus for peritoneal dialysis, the improvements being in the area of patient safety and flexibility of utilization.

Accordingly, this invention provides a dialysis apparatus comprising:
first means for supplying dialysis fluid,
second means for measuring a predetermined quantity of dialysis fluid,
third means for detecting a minimum quantity of dialysis fluid,
a catheter,
structural means supporting said first means above said second means, said second means above said catheter and said third means below said catheter,
a first fluid flow path interconnecting said first and second means,
a second fluid flow path interconnecting said second means and said catheter,
a third fluid flow path interconnecting said catheter and said third means,
a fourth fluid flow path for fluid draining from said third means, valve means for selectively
  (i) blocking said first and third paths while leaving said second and fourth paths open,
  (ii) blocking said second and third paths while leaving said first and fourth paths open, and
  (iii) blocking said second and fourth paths while leaving said first and third paths open,
and timer/computer means for dictating the time intervals during which the valve means is in modes (i), (ii), and (iii).

Further, this invention provides a method of peritoneal dialysis, which includes the steps:
providing a dialysis apparatus which includes first means for supplying dialysis fluid, second means for measuring a predetermined quantity of dialysis fluid, third means for detecting a minimum quantity of dialysis fluid, a catheter into the peritoneal cavity of a patient, structural means supporting said first means above said second means, said second means above said catheter, and said third means below said catheter, means defining a first fluid flow path interconnecting said first and second means, means defining a second fluid flow path interconnecting said second means and said catheter, means defining a third flow path interconnecting said catheter and said third means, and means defining a fourth fluid flow path for fluid draining from said third means;
in rotational sequence:
  (i) blocking said first and third paths while leaving said second and fourth paths open, whereby to allow dialysis fluid in said second means to pass by gravity along said second flow path into the peritoneal cavity of the patient and simultaneously to allow dialysis fluid in said third means to pass outwardly along said fourth path;
  (ii) blocking said second and third paths while leaving said first and fourth paths open, whereby to initiate the replenishment of fresh dialysis fluid in the second means from the first means along said first flow path, and simultaneously allowing further drainage of used dialysis fluid from the third means, during which dialysis fluid in the peritoneal cavity of the patient remains there; and (iii) blocking said second and fourth paths while leaving said first and third paths open, whereby fresh dialysis fluid continues to pass along said first path from the first means to the second means, and simultaneously dialysis fluid from the peritoneal cavity of the patient begins to drain along the catheter and said third path into said third means;

mode (i) constituting the fill mode for the patient, mode (ii) constituting the dwell mode for the patient, and mode (iii) constituting the drain mode for the patient.

Two embodiments of this invention are illustrated in the accompanying drawings, in which like numerals denote like parts throughout the several views, and in which:

FIG. 1 is a schematic diagram showing the basic components of a peritoneal dialysis system which are common to this invention and to the prior art;

FIGS. and 2 and 3 are plan and elevational views of the valve means component applicable to either embodiment of this invention;

Figure 5:
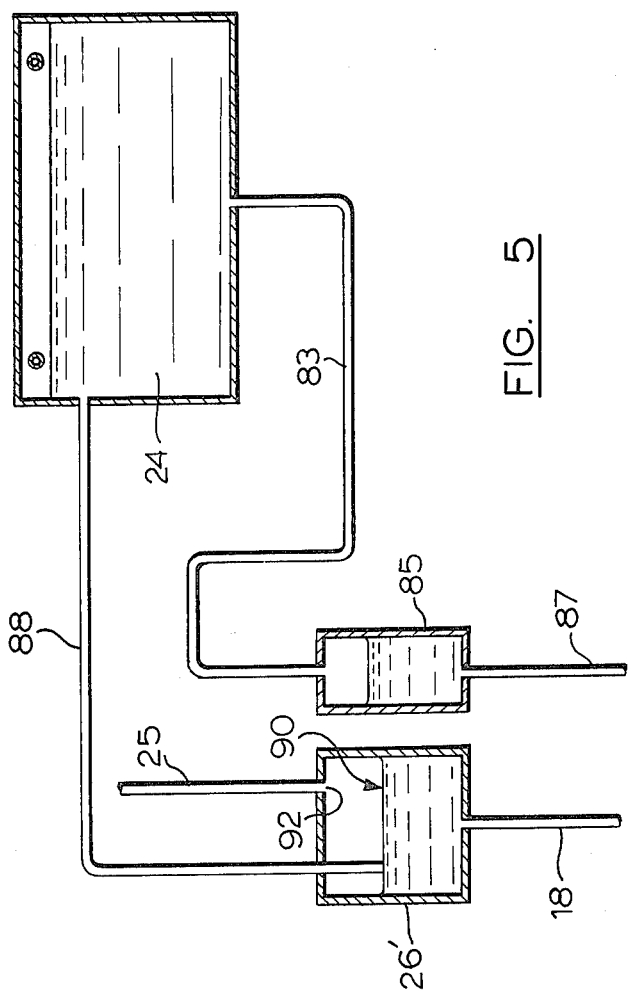
FIG. 5 is a schematic view of a portion of the overall system illustrating the second embodiment of the invention.
Figure 4B:
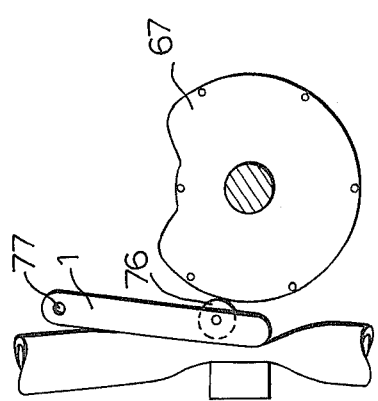
FIGS. 4a to 4d are drawings of cam members employed in the component shown in FIGS. 2 and 3.
Figure 4D:
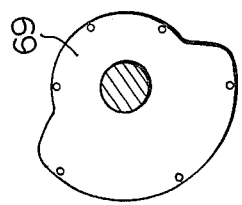
Figure 4A:
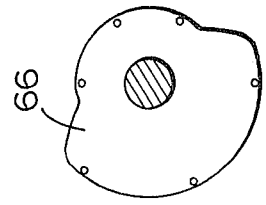
Figure 4C:
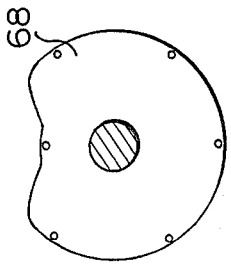

Attention is firstly directed to FIG. 1 in which is illustrated a basic system to which this invention can be applied.

In FIG. 1 is schematically shown a dialysis apparatus 10 which comprises first means 12 for supplying dialysis fluid, second means 14 for measuring a predetermined quantity of dialysis fluid, third means 16 for detecting a minimum quantity of dialysis fluid, and a catheter 18 adapted to allow dialysis fluid to flow to and from the peritoneal cavity of a patient identified by the letter P.

Flexible tubes are provided for interconnecting the various means just defined, and these include a first tube 21 extending downwardly from the first means 12, a secont tube 22 extending downwardly from the second means 14, a third tube 23 extending from a receptacle 24 forming a part of the third means 16 which is adapted to detect a minimum quantity of dialysis fluid, a tube 25 extending from the junction of tubes 21 and 22 into a drip chamber 26, a tube 27 communicating with tube 23 and also extending into the drip chamber 26, a tube 29 also communicating with tube 23 and extending into a separate drip chamber 32 from the bottom end of which a drainage tube 23 extends, and a tube 34 from the bottom of drip chamber 26 to the catheter 18.

A stand 35 having a base 36 with wheels 37 suspends the first means 12 from its upper end, the second means 14 at a position lower down than that of the first means 12, and the third means 16 at a position further down from that of the second means 14. Although the structural connection between the stand 35 and the means 16 has not been shown, it is to be understood that the support for the latter would be attached to the stand 35. Since FIG. 1 is somewhat schematic, it is difficult to show all necessary connections in accurate configuration.

Turning to the third means more particularly, it will be seen that this includes a lever means 40 adapted to pivot on a fulcrum 42, the lever means 40 suspending the fluid container or receptacle 24 at its one end 43 against a predetermined lift weight 45 at the other end.

A microswitch 47 is provided, which is fixed to the rightward end of the lever means 40, and is adapted to contact a fixed surface 48 upon upward movement. Another fixed surface 49 limits the downward movement of the end of the lever means 40. Both surfaces 48 and 49 are supported from the stand 35 by means not shown. When the liquid content of the fluid container 24 exceeds the lift weight 45 and causes the lever means 40 to shift in a counter-clockwise direction about the fulcrum 42, the microswitch 47 is activated. When the container 24 with its contents does not exceed the lift weight 45, the lever means 40 tends to move in a clockwise direction as seen in the figure, thereby de-activating microswitch 47.

The various tubes which have been described define a number of flow paths as follows. A first fluid flow path interconnects the first means 12 and the second 14, and consists of the first tube 21 and the second tube 22. A second fluid flow path interconnects the second means 14 and the catheter 18, this second flow path including the second tube 22, tube 25 and the tube 34. A third fluid flow path interconnects the catheter and the container 24 of the third means 16, this third flow path including the tube 34, the tube 27 and the tube 23. Finally, a fourth fluid flow path allows fluid to drain from the container 24 of the third means 16, and includes the tube 23, the tube 29, and the drainage tube 33.

Valve means shown schematically in FIG. 1 and identified by the numeral 50 is adapted selectively to control the first to fourth fluid flow paths defined above, by constricting or leaving unconstricted the tubes 21, 27 25 and 29.

The apparatus of FIG. 1 is adapted to operate in three different modes. These may be identified as the FILL mode, the DWELL mode and the DRAIN mode.

When the apparatus of FIG. 1 is in the FILL mode, tubes 21 and 27 are blocked, while tubes 25 and 29 remain open. In FIG. 1, the associated clamp locations are identified by numerals 1, 2, 3, and 4, and it is to be understood that when any of the numbered clamps are closed, the associates tube is nipped tight and blocked.

FIG. 2, to which attention is now directed, shows the valve means 50 to larger scale, with the components accurately represented rather than schematically illustrated. It can be seen that in FIG. 2 the tubes 21 and 27 are closed by the clamps 1 and 2 (the structure of which will be explained shortly), while the tubes 25 and 29 are allowed to remain open by the clamps 3 and 4. As previously stated, this represents the FILL mode for the apparatus.

When the apparatus of FIG. 1 is in the FILL mode, dialysis fluid is prevented from passing out of the first means 12, and is prevented from passing along the tube 27. However, fluid is permitted to pass from the second means 14 along tubes 22 and 25, through the drip chamber 26 and along the catheter 18 into the peritoneal cavity of the patient P. Also, fluid is permitted to drain out of the container 24 along tube 23, tube 29, drip chamber 32 and drainage tube 33.

Following the FILL mode, the timing of which will be discussed subsequently, the apparatus goes into the DWELL mode, in which clamps 1 and 4 are opened and clamps 2 and 3 are closed. In this mode, the blockage of tubes 27 and 25 by clamps 2 and 3 respectively prevent dialysis fluid from moving along the tube 34, and thereby maintain the dialysis fluid in the peritoneal cavity of the patient P. At the same time, the opening of tube 21 by clamp 1 allows fluid to flow from the first means 12 into the second means 14, and also allows fluid to continue to drain out of the container 24 along tubes 23 and 29, drip chamber 32 and drainage tube 33.

When the DWELL mode has been completed, the DRAIN mode is initiated, in which clamps 3 and 4 are closed while clamps 1 and 2 are open. In this mode dialysis fluid continues to drain from the first means 12 into the second means 14, and fluid in the peritoneal cavity of the patient P is allowed to pass along tube 34, tube 27 and tube 23 into the container 24.

Before describing the timing sequence for the apparatus of FIG. 1, it is necessary to point out that the second means 14 which measures a predetermined quantity of dialysis fluid is intended to heat the dialysis fluid up to the required temperature, which normally is 37° C. For this purpose, a heater element 53 shown schematically in FIG. 1 is adapted to do the heating.

Also shown schematically in FIG. 1 is a a timer/computer means 56 which is adapted to dictate the time intervals during which the valve means 50 is in the FILL mode, the DWELL mode and the DRAIN mode. Electrical wires connecting the timer/computer means 56 with the microswitch 47 and with the valve means 50 have been drawn in broken lines.

We have already described the condition of the clamps 1, 2, 3 and 4 during the FILL mode, the DWELL mode and the DRAIN mode of this apparatus. It is now described to explain the timing sequence as controlled by the timer/computer means 56.

Prior to the FILL mode, it is assumed that dialysate has previously entered the second means 14 and has been heated therein by the element 53 to the required temperature. The dialysis fluid in the second means 14 is thus ready to be passed into the peritoneal cavity of the patient.

When the FILL mode is initiated, the timer/computer 56 begins to count the time, and after a selectable period, which typically would be about 5 minutes, it would automatically switch to the DWELL mode. In the DWELL mode, with clamps 1 and 4 open and clamps 2 and 3 closed, fresh, cold dialysate is allowed to pass from the first means 12 into the second means 14 thus filling the heater bag. Also, waste dialysate from the container 24 continutes to drain into a waste container through the drainage tube 33. The DWELL mode would be set to occupy a given length of time, which normally would be about 25 minutes, and at the end of the DWELL mode the timer/computer means 56 would automatically switch to the DRAIN mode, unless a particular warning signal were to occur, now to be described. All during the FILL mode and DWELL mode, dialysate fluid which had previously passed into the container 24 from the peritoneal cavity of the patient (in the preceding DRAIN mode) will be emptying along tubes 23 and 29, drip chamber 32 and drainage tube 33. At the beginning of this drainage operation, the total weight of the container 24 and its contents will exceed the lift weight 45, and the rightward end of the lever means 40 will have moved upwardly to activate microswitch 47. As the dialysate drains from the container 24, however, the point will be reached at which the weight 45 exceeds the weight of the container 24 plus its contents, and this will cause the lever means 40 to swing in the clockwise direction so that its rightward end rests against surface 49, thus de-activating the microswitch 47. If there is some problem with the drainage of dialysate from the container 24, such that the point of shift for the lever means 40 is not reached, i.e., such that the rightward end of the lever means 40 does not come down against the surface 49 prior to the end of the preset time for the combined FILL and DWELL modes, the timer/computer means 56 will detect this fact, and will activate an alarm signal to inform the user that the container 24 has not properly drained within the allotted time. It is obviously quite important to empty or substantially empty the container 24 when the apparatus is in the FILL and DWELL modes, for otherwise the following DRAIN mode would not allow all of the dialysate to flow out of the peritoneal cavity of the patient due to the fact that there would still be some remaining fluid in the container 24.

Since the DWELL mode of nominally 25 minutes precedes the DRAIN mode also nominally of 25 minutes, and since the heating of cold dialysate in the second means 14 is commenced during the DWELL mode, it is possible to provide up to 50 minutes of heating time to ensure that the dialysate in the second means 14 will rise to the required temperature. Experience shows that typically 30 minutes is sufficient to raise the dialysate temperature from room temperature to body temperature. This means that the drain time may be selectively reduced to as low as 15 minutes if this is desired, for fast dialysis treatment.

The latter improvement is achieved because the present invention introduces the concept of three modes of operation (FILL, DWELL and DRAIN) in conjunction with four individually occluding cams, rather than the very restricted two-mode operation utilized in the prior art. By providing an independent FILL mode, the patient fluid intake volume is evenly regulated simply by selecting the fill time. This is difficult or impossible with the conventional prior art apparatus.

Returning now to FIG. 1, the utilization of the microswitch 47 will now be described. When the apparatus is in the DRAIN mode, in which dialysate is draining from the peritoneal cavity of the patient P along tube 34 and ultimately into the container 24, the lever means 40 is initially in a condition in which its rightward end is downward against the surface 49, and the microswitch 47 is de-activated. As fluid continues to enter the container 24, the point is ultimately reached where the total weight of the container 24 plus its contents exceeds that of the lift weight 45, and the lever means 40 swings in the counterclockwise direction to activate the microswitch 47. If by the end of a preset time the lever means 40 has not shifted in the clockwise direction to activate the microswitch 47, the timer/computer means 56 will detect this fact, and will activate a signal, which may be an alarm, a light, or a combination of these, to indicate that the patient drainage has not proceeded properly.

In addition to the two alarm system described above, this apparatus is provided with a high dialysate temperature alarm operating on the thermistor principle and detecting the temperature in the second means 14, a "power-off alarm" intended to draw attention in case of power failure or a blown fuse, a "low-temperature alarm" which is set to detect, at any time, extreme low temperature dialysate and to switch off the apparatus when such is detected, and a thermistor failure alarm which is a back-up alarm to ensure that the thermistor or thermostat detecting the temperature of dialysate fluid in the second means 14 works correctly.

Attention is now directed specifically to FIG. 2, for a description of the valve or clamping means 50. This component includes a motor 60, three reed switches 61, 62 and 63, a magnet 65, four cams 66, 67, 68 and 69, and four tube occluding fingers or clamps which have already been identified by numerals 1, 2, 3 and 4.

The motor 60 is adapted to rotate a shaft 70 at slow speed through a speed-reducing gear system (not shown) contained in housing 71. The magent 65 is mounted on a disc 73 which is securely attached to the shaft 70. The four cams 66–69 are also securely mounted on the shaft 70 and rotate therewith. Thus, when the motor 60 is activated, the shaft 70 rotates the four cams 66–69 and the disc 73 together. When the motor is activated, it causes the magnet to rotate past the three reed switches 61, 62 and 63, the positions of which are best seen in FIG. 3. The reed switches are positioned to correspond to the selected cam positions are the FILL, DWELL and DRAIN modes. When the actuating magnet lines up with one of the reed switches, the reed switch closes and a signal is generated for the timer/computer means 56. If the closed reed switch corresponds to the selected state (FILL, DWELL or DRAIN), the logic utilized by the timer/computer means 56 deactivates the motor 60 and arrests the shaft 70 in that position.

When the motor 60 is in motion and the actuating magnet 65 is searching for the appropriate reed switch, the four cams 66–69 are also in rotation. Each cam is adapted to push against the lower end of a respective tube-occluding finger 1–4, and each of the fingers has a follower wheel 76 mounted at the lower end away from a fixed pivot pin 77 at the upper end (see FIG. 4B). As seen in FIGS. 4A–4D, the cams 66–69 have suitable contours to permit the occluding or clamping of the tubes in accordance with the FILL, DWELL and DRAIN modes described earlier.

In FIG. 2, the clamping valve means 50 includes a bar 79 which presents a fixed surface 80 against which the tubes are adapted to be squeezed by the fingers 1–4.

Figure 6:
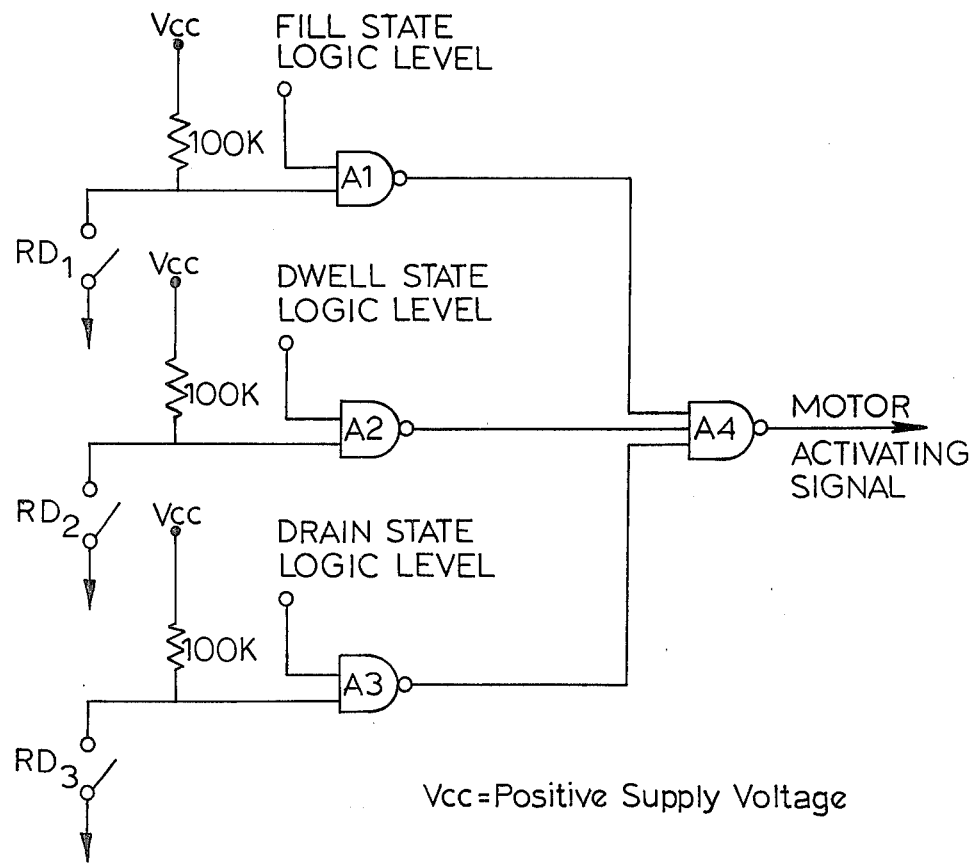
FIG. 6 is a schematic view of the motor logic utilized.

FIG. 6 shows the motor logic arrangement utilized by the apparatus of this invention. The logic arrangement is responsible for controlling the FILL, DWELL and DRAIN modes, and it is such that only one of these three signals is high at any given time. The high signal corresponds to the active state.

In FIG. 6, the three signals for FILL, DWELL and DRAIN modes are applied to the nand gates A1, A2 and A3 respectively. The property of nand gates is such that if all inputs are at high logic levels, the output is a low logic level and if any of the inputs is a low level, the output is at a high level. If the output of either A1, A2 or A3 goes low, the output of A4 goes high. The high output of A4 activates the motor which runs until the output of A4 goes low.

RD1, RD2 and RD3 are the reed switches corresponding to the FILL, DWELL and DRAIN modes respectively. If any one of these switches is closed, the corresponding input to the respective gate A1, A2 or A3 goes low.

When the FILL state is manually or automatically selected, the FILL state input to A1 goes high, and the DWELL state input to A2 and DRAIN state input to A3 both go low. The low inputs to A2 and A3 cause the outputs of gates A2 and A3 to go high. Since the FILL state input to A1 is high and the reed switch RD1 is open, the two inputs of gate A1 are both high and its output goes low. This causes the output of A4 to go high. The motor is then activated and the actuating magnet is set in motion. When the magnet lines up with the reed switch RD2 corresponding to the DWELL state, the switch is closed causing one input of A2 to go low. However, the output of A2 is already high due to the low DWELL state input to A2 and the closing of the reed switch RD2 does not change anything. The output of A4 remains at the high level and the motor keeps on running. Because the DRAIN state signal input to A3 is also low, when the actuating magnet closes the reed switch RD3, the high logic output of A3 and A4 remain unaffected and the motor keeps on running.

When the actuating magnet closes the reed switch RD1, one input to gate A1 goes low causing the output of A1 to go high from low. The three inputs to A4 then all become high causing the output of A4 to change state from high to low, and this deactivates the motor so that the motor stops.

A similar exercise takes place upon selection of either DWELL or DRAIN state, and it will be clear how the logic is able to select the angular position of the cams according to the state which is selected.

Attention is now directed to FIG. 5, which shows certain improvements in the details of the overall system of FIG. 1, which may be looked upon as a further embodiment of the invention.

Earlier in this description a fourth fluid path has been defined as one which permits liquid to drain from the container 24 of the means 16 to a waste disposal. In FIG. 1, the fourth fluid path includes tube 23, tube 29, drip chamber 32 and drainage tube 33. In the embodiment of FIG. 1, there is a risk of contamination of fresh dialysate with toxins or organisms contained in the used dialysate in container 24, for two reasons. The first reason relates to the fact that the same tube 23 is used (in the FIG. 1 embodiment) both to conduct dialysate to container 24 and to drain dialysate from 24 and finally through the drainage tube 33. This will mean that tube 23 will have a tendency to store toxic materials, active organisms, etc., and it is possible that these contaminants could pass along tube 27 and into drip chamber 26, from where during the fill mode they could mix with the fresh dialysate from the second means 14 entering the peritoneal cavity of the patient. The modification of the present invention shown in FIG. 5 attempts to eliminate the risk of contamination of fresh dialysate by firstly providing a separate drainage tube 83 from the bottom of the container 24, feeding into its own separate drip chamber 85 and thence out a separate drainage tube 87. The passage of dialysate from the peritoneal cavity of the patient into the container 24 takes place through a modified drip chamber 26' into which the tube 25 enters in the usual way (the same as tube 25 in FIG. 1), and into which a separate tube 88 extends, linking the drip chamber 26' with the container 24. The tube 88 becomes part of the previously-defined third flow path, along which dialysate flows from the peritoneal cavity of the patient into the container 24. It will be noted that the tube 88 extends partway downwardly into the modified drip chamber 26'. This structure will ensure that the liquid level 90 inside the modified drip chamber 26' does not rise up to touch the mouth 92 of the tube 25. Since dialysate flows only in one direction along tube 88 (from the drip chamber 26' to the container 24), it is not possible for contaminants, toxins, organisms and so forth, to successfully migrate the whole distance from the container 24 to the drip chamber 26' because these materials would have to move upstream against the consistent flow in the opposite direction. This is not the case for the first embodiment shown in FIG. 1, in which dialysate flows in both directions through the tube 23, depending upon the mode of operation of the apparatus at the time.

A further safeguard for the fresh, unused dialysate in the first means 12 and the second means 14 is provided by ensuring the spacing between the mouth 92 of the tube 25 and the liquid level 90 in the modified drip chamber 26'. Even if the liquid within the modified drip chamber 26' were to become contaminated by materials somehow managing to move against the flow in tube 88, the same would be confined to the modified drip chamber 26' and the catheter 18, and would not be able to contaminate the fresh, unused dialysate in the means 12 and 14. This would mean that further steps in the ongoing FILL, DWELL and DRAIN sequence would flush any contaminants out of the modified drip chamber 26' and the catheter 18, and restore the system to the required safety level.

We claim:

1. A dialysis apparatus comprising:
first means for supplying dialysis fluid,
second means for measuring a predetermined quantity of dialysis fluid,
third means for detecting a minimum quantity of dialysis fluid,
a catheter,
structural means supporting said first means above said second means, said second means above said catheter and said third means below said catheter,
a said fluid flow path interconnecting said first and second means,
a second fluid flow path interconnecting said second means and said catheter,
a third fluid flow path interconnecting said catheter and said third means,
a fourth fluid flow path for fluid draining from said third means,
valve means for selectively
 (i) blocking said first and third paths while leaving said second and fourth paths open,
 (ii) blocking said second and third paths while leaving said first and fourth paths open, and
 (iii) blocking said second and fourth paths while leaving said first and third paths open,
and timer/computer means for dictating the time intervals during which the valve means is in modes (i), (ii) and (iii).

2. The apparatus claimed in claim 1, in which said third means includes a lever means suspending a fluid container against a predetermined lift weight, the fluid container being adapted to receive the fluid moving along said third path, whereby in mode (iii), if within a preset time the weight of fluid in said container does not exceed said lift weight to cause the lever means to shift and activate a signal-producing device, the failure to produce the signal activates a patientdrain alarm.

3. The apparatus claimed in claim 1, in which said third means includes a lever means suspending a fluid container against a predetermined lift weight, the fluid container being adapted to receive the fluid moving along said third path, whereby in modes (i) and (ii), if after a preset time the fluid container has not emptied sufficiently to cause the lever means to shift in the direction of said lift weight, a signal is produced to activate a waste-bag alarm.

4. The apparatus claimed in claim 1, in which said second means includes means for heating dialysis liquid contained therein to a predetermined temperature.

5. The apparatus claimed in claim 1, in which said first to fourth flow paths are defined by flexible tubes, and in which said valve means includes cam-operated means for pinching and thus closing said tubes.

6. The apparatus claimed in claim 1, in which at least parts of said first to fourth flow paths are defined by four flexible tubes, and in which said valve means includes a fixed surface, four finger members each pivoted at one end about a common axis and each having its other end free to swing closer to or farther from said fixed surface, said four tubes passing between said surface and said four finger members respectively whereby each finger member is adapted to bear against one of the tubes, a cam shaft, four cams mounted on said cam shaft with each cam adapted to urge one of the finger members closer to the fixed surface to allow it to recede therefrom, means for rotating said cam shaft selectively.

7. The apparatus claimed in claim 1, in which the valve means includes four individually occluding cam means for closing and opening tubes defining the first to fourth flow paths.

8. The apparatus claimed in claim 6, in which said cam shaft carries a magnetic means spaced from the cam shaft axis and rotating with the cam shaft, three normally open magnetic reed switches mounted in fixed positions and adapted to be closed by the field from said magnetic means as the latter rotates around with the cam shaft, the closing of each reed switch sending an electrical signal adapted to halt the rotation of the cam shaft.

9. The apparatus claimed in claim 1, in which the fourth flow path is completely separated and distinct from the other three flow paths.

10. The apparatus claimed in claim 9, in which the fourth flow path includes a drip chamber.

11. The apparatus claimed in claim 1, in which the second and third flow paths have a portion of each in common and other portions of each separate from each other, the common portion being separated from the other portions by a drip chamber.

12. The apparatus claimed in claim 11, in which said other portion of the third flow path is constituted by a tube of which part extends downwardly into said drip chamber so as to limit the uppermost position of the liquid level therein when the third flow path is open and the second flow path is closed, the second flow path being constituted by a tube connected to the drip chamber at a location above said uppermost position of the liquid level therein, whereby contamination of the unused dialysis liquid from the used dialysis liquid is restrained.

13. The apparatus claimed in claim 2, in which said second means includes means for heating dialysis liquid contained therein to a predetermined temperature; in which at least parts of said first to fourth flow paths are defined by four flexible tubes; and in which said valve means includes a fixed surface, four finger members each pivoted at one end about a common axis and each having its other end free to swing closer to or farther from said fixed surface, said four tubes passing between said surface and said four finger members respectively whereby each finger member is adapted to bear against one of the tubes, a cam shaft, four cams mounted on said cam shaft with each cam adapted to urge one of the finger members closer to the fixed surface or allow it to recede therefrom, means for rotating said cam shaft selectively.

14. The apparatus claimed in claim 13, in which said cam shaft carries a magnetic means spaced from the cam shaft axis and rotating with the cam shaft, three normally open magnetic reed switches mounted in fixed positions and adapted to be closed by the field from said magnetic means as the latter rotates around with the cam shaft, the closing of each reed switch sending an electrical signal adapted to halt the rotation of the cam shaft.

15. The apparatus claimed in claim 14, in which the fourth fluid path is completely separated and distinct from the other three flow paths, and includes a drip chamber.

16. The apparatus claimed in claim 15, in which the second and third flow paths have a portion of each in common and other portions of each separate from each other, the common portion being separated from the other portions by a drip chamber, said other portion of the third flow path being constituted by a tube of which part extends downwardly into said last-mentioned drip chamber so as to limit the uppermost position of the liquid level therein when the third flow path is open and the second flow path is closed, the second flow path being constituted by a tube connected to the drip chamber at a location above said uppermost position of the liquid level therein, whereby contamination of the unused dialysis liquid from the used dialysis liquid is restrained.

17. A method of peritoneal dialysis, which includes the steps:
providing a dialysis apparatus which includes first means for supplying dialysis fluid, second means for measuring a predetermined quantity of dialysis fluid, third means for detecting a minimum quantity of dialysis fluid, a catheter into the peritoneal cavity of a patient, structural means supporting said first means above said second means, said second means above said catheter, and said third means below said catheter, means defining a first fluid flow path interconnecting said first and second means, means defining a second fluid flow path interconnecting said second means and said catheter, means defining a third fluid flow path interconnecting said catheter and said third means, and means defining a fourth fluid flow path for fluid draining from said third means;

in rotational sequence:

(i) blocking said first and third paths while leaving said second and fourth paths open, whereby to allow dialysis fluid in said second means to pass by gravity along said second flow path into the peritoneal cavity of the patient and simultaneously to allow dialysis fluid in said third means to pass outwardly along said fourth path;

(ii) blocking said second and third paths while leaving said first and fourth paths open, whereby to initiate the replenishment of fresh dialysis fluid in the second means from the first means along said first flow path, and simultaneously allowing further drainage of used dialysis fluid from the third means, during which dialysis fluid in the peritoneal cavity of the patient remains there; and (iii) blocking said second and fourth paths while leaving said first and third paths open, whereby fresh dialysis fluid continues to pass along said first path from the first means to the second means, and simultaneously dialysis fluid from the peritoneal cavity of the patient begins to drain along the catheter and said third path into said third means;

mode (i) constituting the fill mode for the patient, mode (ii) constituting the dwell mode for the patient, and mode (iii) constituting the drain mode for the patient.

18. The method claimed in claim 17, in which dialysis fluid in said second means is heated.

* * * * *